(12) United States Patent
Baghani et al.

(10) Patent No.: US 10,667,791 B2
(45) Date of Patent: Jun. 2, 2020

(54) ELASTOGRAPHY USING ULTRASOUND IMAGING OF A THIN VOLUME

(75) Inventors: Ali Baghani, Vancouver (CA); Hani Eskandari, Vancouver (CA); Robert N. Rohling, Vancouver (CA); Septimu E. Salcudean, Vancouver (CA)

(73) Assignee: The University of British Columbia, Vancouver (CA)

( * ) Notice: Subject to any disclaimer, the term of this patent is extended or adjusted under 35 U.S.C. 154(b) by 1160 days.

(21) Appl. No.: 14/239,775

(22) PCT Filed: Aug. 17, 2012

(86) PCT No.: PCT/CA2012/000779
§ 371 (c)(1),
(2), (4) Date: Jul. 21, 2014

(87) PCT Pub. No.: WO2013/026141
PCT Pub. Date: Feb. 28, 2013

(65) Prior Publication Data
US 2014/0330122 A1    Nov. 6, 2014

Related U.S. Application Data

(60) Provisional application No. 61/525,378, filed on Aug. 19, 2011.

(51) Int. Cl.
*A61B 8/00* (2006.01)
*A61B 8/08* (2006.01)
*A61B 8/12* (2006.01)
(52) U.S. Cl.
CPC .............. *A61B 8/485* (2013.01); *A61B 8/463* (2013.01); *A61B 8/483* (2013.01); *A61B 8/5223* (2013.01); *A61B 8/0825* (2013.01); *A61B 8/12* (2013.01)

(58) Field of Classification Search
None
See application file for complete search history.

(56) References Cited

U.S. PATENT DOCUMENTS

| 2002/0068870 A1* | 6/2002 | Alam ................. A61B 5/0051 600/446 |
| 2003/0193336 A1 | 10/2003 | Ehman et al. |
| 2003/0216646 A1 | 11/2003 | Angelsen et al. |

(Continued)

OTHER PUBLICATIONS

International Search Report and Written Opinion for PCT/CA2012/000779.

*Primary Examiner* — Patricia J Park
(74) *Attorney, Agent, or Firm* — Oyen Wiggs Green & Mutala LLP

(57) ABSTRACT

The embodiments described herein relate generally to an elastography method and system for obtaining ultrasound images of an excited tissue over a certain time period, then computationally determining one or more mechanical properties of the tissue within a real time refresh rate. This method can perform elastography in real time as only a thin volume of the excited tissue is imaged and processed. The thin volume includes a desired cross-sectional plane of the tissue and at least two adjacent planes that are adjacent to the desired cross-sectional plane. A maximum number of adjacent planes is selected so that a computer system is capable of computationally determining mechanical properties within a real time refresh rate.

34 Claims, 13 Drawing Sheets

(56) References Cited

U.S. PATENT DOCUMENTS

| | | | |
|---|---|---|---|
| 2003/0220556 A1* | 11/2003 | Porat | A61B 5/0051 600/407 |
| 2005/0119568 A1* | 6/2005 | Salcudean | A61B 8/08 600/437 |
| 2006/0173319 A1* | 8/2006 | Sumi | A61B 8/08 600/437 |
| 2007/0121097 A1 | 5/2007 | Boillot | |
| 2007/0161891 A1 | 7/2007 | Moore et al. | |
| 2009/0216131 A1 | 8/2009 | Chase et al. | |
| 2009/0324040 A1* | 12/2009 | Lindop | G01S 7/52042 382/131 |
| 2010/0138163 A1 | 6/2010 | Gallippi et al. | |
| 2010/0251820 A1 | 10/2010 | Righetti et al. | |
| 2010/0312110 A1* | 12/2010 | Suzuki | A61B 5/02007 600/443 |
| 2011/0130660 A1* | 6/2011 | Cloutier | A61B 5/02007 600/438 |
| 2012/0157831 A1* | 6/2012 | Waki | A61B 8/08 600/427 |
| 2012/0215101 A1* | 8/2012 | Maleke | A61B 5/055 600/438 |

* cited by examiner

ELASTOGRAPHY USING ULTRASOUND IMAGING OF A THIN VOLUME

CROSS-REFERENCE TO RELATED APPLICATIONS

This application claims priority to a U.S. provisional application having Ser. No. 61/525,378, filed on Aug. 19, 2011, the entirety of which is herein incorporated by reference.

FIELD OF INVENTION

This invention relates generally to medical imaging, and in particular to elastography using ultrasound imaging of a thin volume of a subject such as tissue to determine viscoelastic properties of the subject.

BACKGROUND

Elastography generally refers to methods of imaging mechanical properties of tissue such as elasticity, viscosity, relaxation time, shear modulus, porosity, etc. Elastography is generally carried out in four steps:
1. exciting the tissue by causing some form of deformation or movement in the tissue;
2. observing and recording with a medical imaging device a series of images depicting the motion of different locations in the tissue over an interval of time;
3. estimating the displacements of the tissue at the different locations and time instances from the series of images; and
4. estimating mechanical properties of the tissue such as elasticity and viscosity from the estimated displacements.

Numerous elastography systems have been proposed in the art by combining different types of excitation, with different imaging modalities. Known imaging modalities include ultrasound and magnetic resonance imaging (MRI), as well as optical coherence tomography (OCT) and x-ray computed tomography (CT). Different methods have also been proposed for estimating the displacements, and estimating elasticity and viscosity from the estimated displacements.

The majority of the magnetic resonance elastography (MRE) methods in the art use steady-state excitation, although transient excitation has also been studied for use in MRE. The majority of the ultrasound elastography methods in prior art use transient excitation, although steady-state excitation has also been studied.

Compared to MRI, OCT or CT, ultrasound imaging has certain advantages, such as lower cost, lighter weight and easier operation. However, existing real-time ultrasound elastography systems that provide imaging of tissue properties use techniques that are computationally intensive and which require sophisticated and expensive computing hardware, or which acquire images only in a 2D imaging plane. Such 2D measurements introduce errors or diminish the ability to measure the absolute value of elasticity, and instead measure just relative variations throughout an image. Therefore, existing ultrasound elastography systems using probes which only acquire data in a 2D imaging plane tend to produce inaccurate measurements.

BRIEF SUMMARY OF THE INVENTION

According to one aspect of the invention, there is provided an elastography method for imaging at least one mechanical property of a tissue in a desired cross-sectional plane of the tissue. The method comprises: applying a steady-state vibration to the tissue to generate tissue displacements in the tissue; ultrasound imaging a thin volume of the tissue over a time period by acquiring a set of image data representing the thin volume over the time period including said desired cross-sectional plane and at least two planes adjacent to the desired cross-sectional plane; computationally estimating a plurality of phase-synchronized displacements over the time period for a plurality of spatial points in the thin volume wherein at least one spatial point is located on each of the cross-sectional plane and the adjacent planes; and computationally determining the at least one mechanical property of the tissue on the desired cross-sectional plane by using the plurality of phase-synchronized displacements. The number of adjacent planes is selected such that the at least one mechanical property of said tissue can be computationally determined within a real time refresh rate which can be defined as being at least one new frame per five seconds. The at least one mechanical property can include any one or more properties selected from: absolute elasticity, absolute shear modulus, absolute shear wave speed, and absolute viscosity. Further, the at least one mechanical property can be calculated from the plurality of phase-synchronized displacements by using any one or a combination of finite element method, local frequency estimators, travelling wave expansion and direct inversion.

According to another aspect of the invention, there is an elastography system for imaging at least one mechanical property of a tissue in a desired cross-sectional plane of said tissue. The system comprises: at least one vibration source configured to generate a steady-state vibration; an ultrasound probe configured to acquire a set of image data over a time period representing a thin volume of a tissue including a desired cross-sectional plane and at least two adjacent planes adjacent to said desired plane; circuitry communicative with the ultrasound probe to receive the image data therefrom and comprising a processor with a memory having programmed thereon steps and instructions for execution by the processor to perform the elastography method described above; and a display device communicative with the circuitry to receive and display one or more images of the desired cross-sectional plane and the determined mechanical property of the tissue within the real-time refresh rate.

The ultrasound probe can be a 3D ultrasound probe. More particularly, the 3D ultrasound probe can be a mechanical 3D probe comprising a 2D probe with an external motion stage. Alternatively, the 3D ultrasound probe can be a multidimensional probe comprising a two dimensional matrix of transducers.

The vibration source can be an electromagnetic voice coil and be mounted on an adjustable arm. The arm can be mounted on an ultrasound machine, a patient bed, or a portable pole. Alternatively, the vibration source can be configured as a hand-held device. Also, the vibration source and the ultrasound probe can be integrated together into single device.

DETAILED DESCRIPTION

Figure 1:
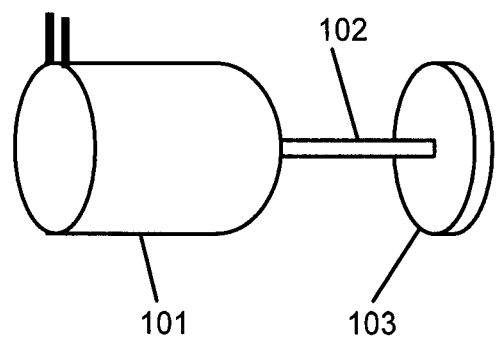
FIG. 1 is a perspective view of a vibration source according to an embodiment of the invention.
Figure 2:
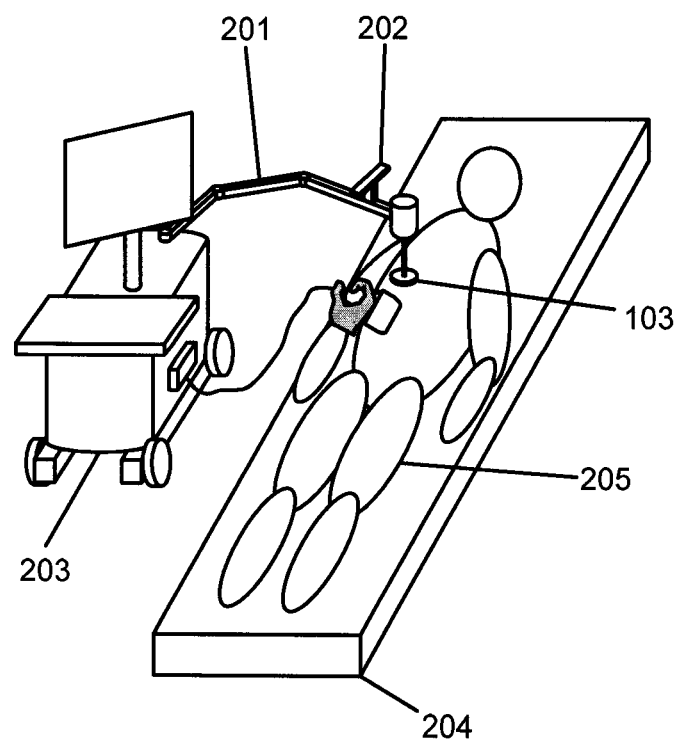
FIG. 2 is a schematic diagram depicting a configuration for imaging a subject with an external probe according to an embodiment of the invention, wherein a vibration source is mounted on an adjustable arm connected to an ultrasound machine.
Figure 3:
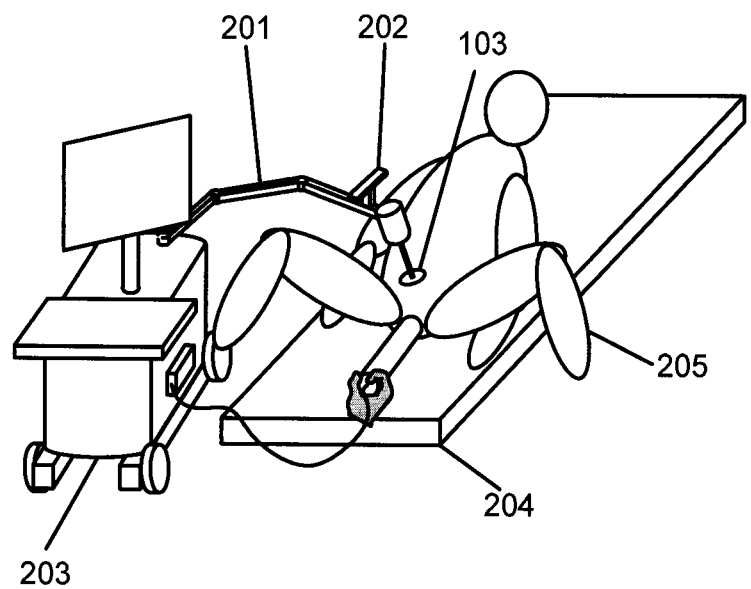
FIG. 3 is a schematic diagram depicting a configuration for imaging a subject with an endo-cavity probe according to an embodiment of the invention, wherein a vibration source is mounted on an adjustable arm connected to an ultrasound machine.
Figure 4:
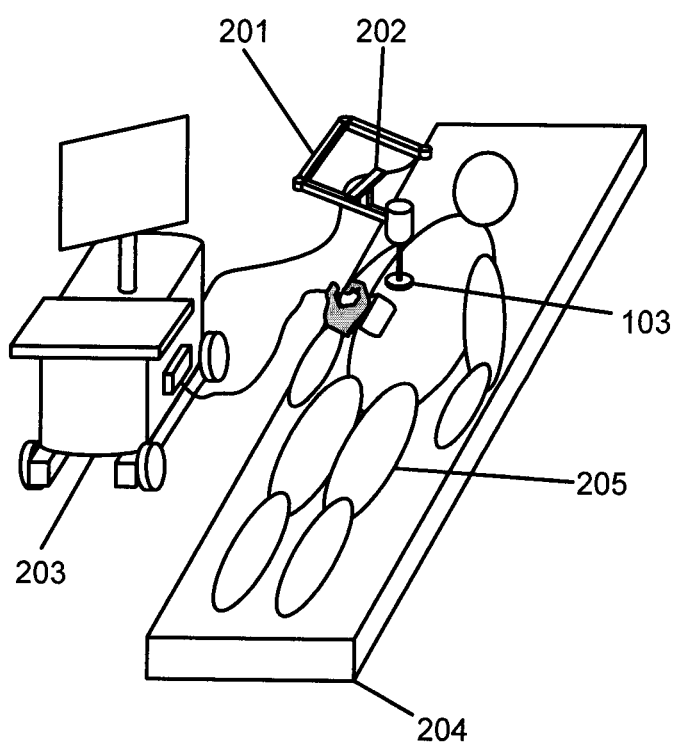
FIG. 4 is a schematic diagram depicting a configuration for imaging a subject with an external probe according to an embodiment of the invention, wherein a vibration source is mounted on an adjustable arm connected to a patient bed.
Figure 5:
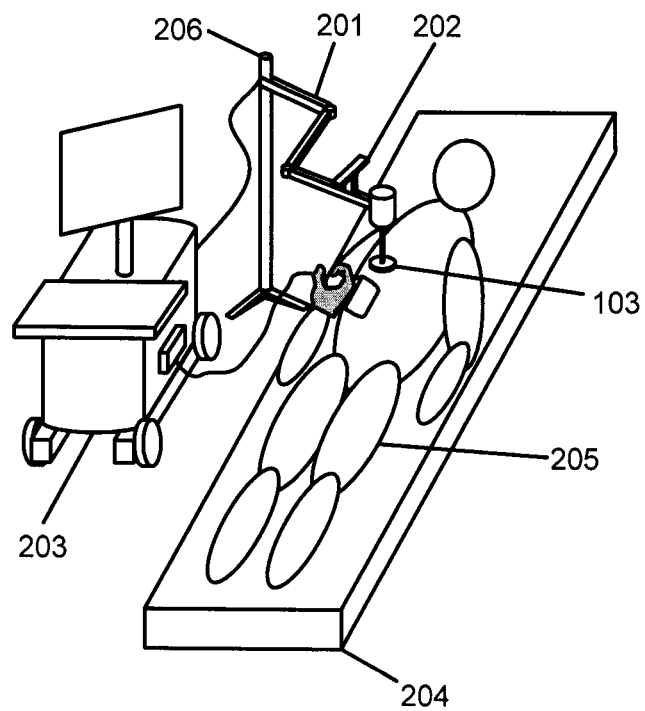
FIG. 5 is a schematic diagram depicting a configuration for imaging a subject with an external probe according to an embodiment of the invention, wherein a vibration source is mounted on an adjustable arm connected to a portable pole.

Directional terms such as "top", "bottom", "upwards", "downwards", "vertically" and "laterally" are used in the following description for the purpose of providing relative reference only, and are not intended to suggest any limitations on how any element is to be displayed during use or relative to an environment.

The embodiments described herein relate generally to an elastography method and system for obtaining ultrasound images of an excited tissue over a certain time period, then computationally determining one or more mechanical properties of the tissue within a real time refresh rate. This method can perform elastography in real time as only a thin volume of the excited tissue is imaged and processed. The thin volume includes a desired cross-sectional plane of the tissue and at least two planes that are adjacent to the desired cross-sectional plane. A maximum number of adjacent planes is selected so that a computer system is capable of computationally determining mechanical properties within a real time refresh rate. In this context, "adjacent" means spaced from and beside the desired cross-sectional plane and in particular, a suitable adjacent plane can be immediately beside the desired cross-sectional plane or have one or more other planes in between it and the desired cross-sectional plane. Also in this context, a real time refresh rate is defined to be at least one new frame per five seconds.

The method generally involves: exciting the tissue to be imaged using a vibration source that can provide a steady state vibration; acquiring ultrasound images of the excited tissue in the form of radio frequency (RF) data in at least two different times over a selected time period; estimating the displacement of the excited tissue from the RF data, which comprises estimating phase-synchronized displacements over the time period for a plurality of spatial points in the ultrasound images; and determining a mechanical property of the tissue such as absolute elasticity and viscosity from the phase-synchronized displacements. Each of these steps are described in more detail below.

The use of measurements of the displacements over a volume is beneficial because it allows the measurement of the spatial wavelength to be performed in all three spatial directions. The speed of the imaging process is proportional to the size of the volume, so a smaller volume is beneficial because it achieves faster imaging rates. The minimum number of data points in any of the spatial directions required to calculate the spatial wavelength is three-two data points only define a line and therefore cannot be used to estimate the spatial wavelength of a waveform composed of sinusoids. Three data points allow a curvature measurement to be made. In other words, three data points allow the second spatial derivative to be calculated, which can be used for measuring the spatial wavelength.

Excitation Generation

Referring now to FIGS. 1 to 10, different embodiments of a vibration source which can generate steady-state excitations to excite a subject tissue, and means for applying vibrations to a subject are provided for use with the elastography method and form part of a elastography system.

In the embodiment shown in FIG. 1, excitation of the subject tissue is generated by a mechanical vibration source 101 which is capable of generating steady-state excitations in the 2 Hz to 1000 Hz range. The vibration source 101 can be an electromagnetic voice coil, or pneumatically or hydraulically-driven. A rod 102 and pad 103 are used to transfer the vibration to the tissue.

Figure 6:
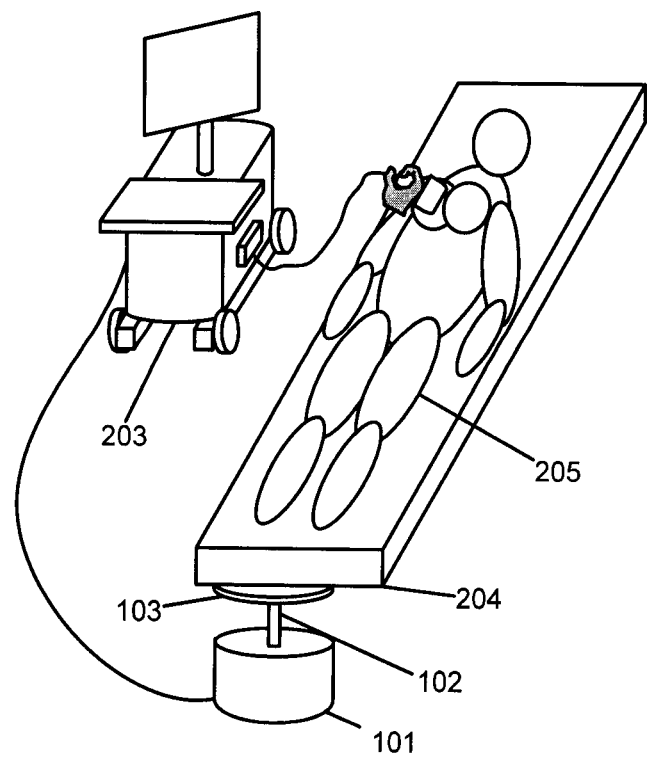
FIG. 6 is a schematic diagram depicting a configuration for imaging a subject with an external probe according to an embodiment of the invention, wherein a vibration source is directly vibrating a patient bed.

Different configurations for applying the vibration source 101 to a subject and imaging the subject with an ultrasound probe are shown in FIGS. 2 to 6. In these embodiments, the vibration source 101 is mounted on an adjustable arm 201. A handle 202 is provided on the adjustable arm 201. A clinician can adjust the arm 201 by using the handle 202 and positioning a vibration pad 103 in contact with a patient 205 at a desired location and at a desired angle. In the embodiments shown in FIGS. 2 and 3, the arm 201 is mounted on an ultrasound machine 203. In the embodiment shown in FIG. 4, the arm 201 is mountable on a patient bed 204. In the embodiment shown in FIG. 5, the arm 201 is mounted on a portable pole 206. FIG. 6 shows another embodiment wherein the vibration source 101 transmits vibrations to a patient directly through the bed 204 on which the patient is positioned.

Figure 7:
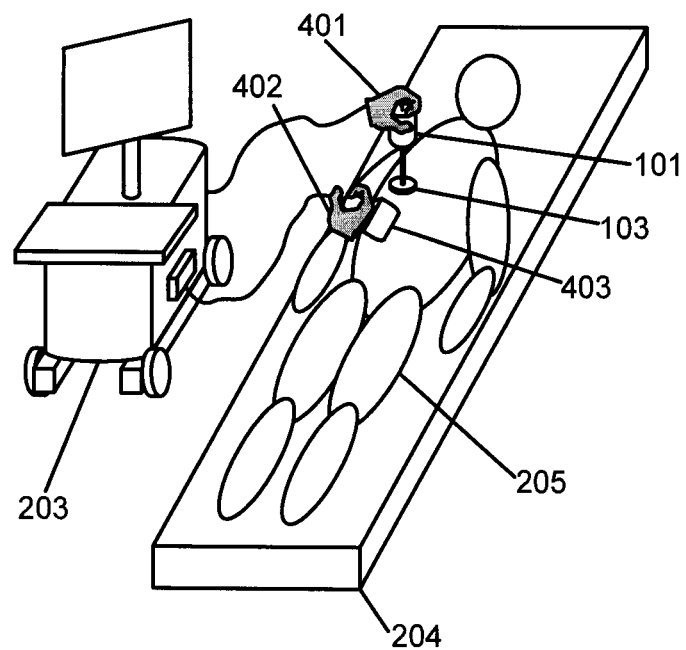
FIG. 7 is a schematic diagram depicting a configuration for imaging a subject with an external probe according to an embodiment of the invention, using a handheld vibration source.

FIG. 7 shows further another embodiment wherein the vibration source 101 is a handheld device. An operator uses one hand 401 to hold the vibration source so that the vibration pad 103 is in contact with the patient, and the other hand 402 to hold the ultrasound probe 403. Alternatively, one operator can hold the vibration source 101, while another operator performs the scan with the ultrasound probe.

Figure 8:
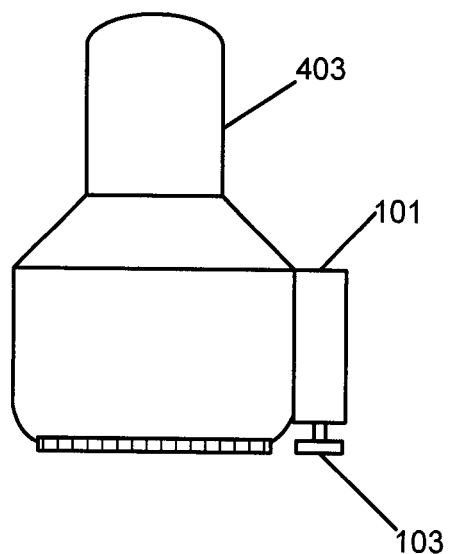
FIG. 8 is a schematic view of an integrated vibration source and ultrasound probe according to an embodiment of the invention, wherein the vibration source is located on the side of the probe.

FIG. 8 is a schematic view of an integrated vibration source and ultrasound probe according to another embodiment of the invention, wherein the vibration source 101 is connected to the ultrasound probe 403 and located on the side or top of the probe 403. Alternatively, two or more vibration sources can be connected to two or more sides of the probe.

Figure 9:
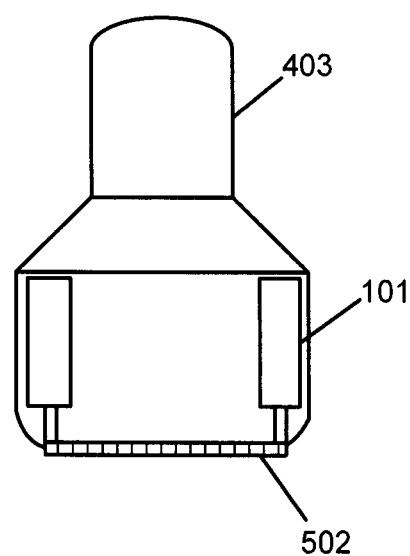
FIG. 9 is a schematic view of an integrated vibration source and ultrasound probe according to an embodiment of the invention, wherein the vibration source is configured to vibrate ultrasound transducers of the probe.

FIG. 9 shows an integrated vibration source and ultrasound probe according to another embodiment of the invention. In this embodiment, at least one vibration source 101 is directly connected to the transducer elements array 502. The generated vibrations are transferred through one or more transducer elements in the array 502 to the tissue, acting as the pad 103 of FIG. 1.

Figure 10:
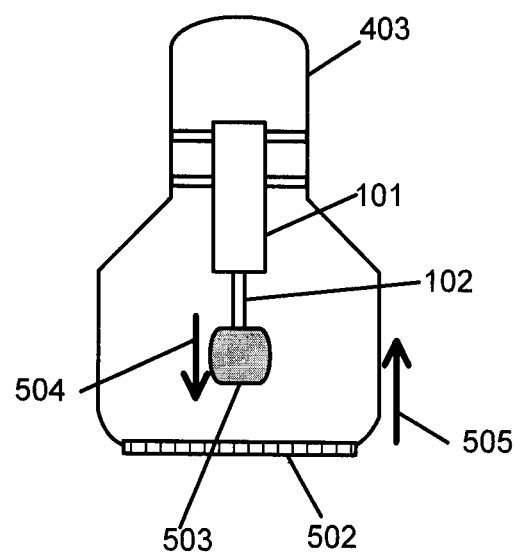
FIG. 10 is a schematic view of an integrated vibration source and ultrasound probe according to an embodiment of the invention, wherein the vibration source is configured to vibrate an inertial mass.

FIG. 10 shows an integrated vibration source and ultrasound probe according to yet another embodiment of the invention. In this embodiment, the vibration source 101 is connected to the probe 403 and a mass 503 is attached to the rod 102. When the mass 503 is moved in the direction 504 by the vibration source 101, the reaction force causes the ultrasound probe 403 to move in an opposite direction 505. The motion in the direction 505 of the probe 403 is transferred to the tissue when the probe 403 comes in contact with the tissue. The mass 503 may be connected to the probe 403 by a spring or a spring-damper system, which can be optimized to achieve a larger motion in a specific frequency range, such as tuning the spring-mass-damper system for a resonance with a specific center frequency and quality factor. Alternatively, the rod 102 of the vibration source 101 can be connected to the probe 403, instead of its body 101, in effect using the vibration source body as the reaction mass and potentially reducing the total probe mass.

In another embodiment, the adjustable arm 201 of the vibration source 101 is connected to the probe 403 instead of the ultrasound machine 203.

In still another embodiment of the invention, excitation is generated internally in the tissue by using acoustic radiation force from an ultrasound machine.

To increase the amplitude of motion in the tissue, any combination of two or more of the excitation sources described herein can be used at the same time.

Steady-State Excitation

The present embodiments of the elastography method utilize steady-state excitations. In this type of excitation, the amplitude and phase of each frequency component of the excitation signal is kept constant over time, and the tissue is studied after the transient effects have dissipated.

In some embodiments of the elastography method, an excitation signal v(t) applied to the vibration source 101 can be in the form of a pure sinusoid at a frequency f:

$$v(t)=a\sin(2\pi ft) \quad (1)$$

When the exciter pad 103 or the probe 403 is vibrating at this frequency, comes in contact with the tissue and is held fixed in space, the vibration pattern in the tissue will reach the steady-state after a short period of time. In this steady state, every point in the tissue will be vibrating at the same frequency f with a sinusoidal pattern, but with differing phases and amplitudes at each location. If the subject is not moving, and the probe and exciter positions are fixed in space, the phase and amplitudes will not change with time, hence the name steady-state. In this setting, the displacement $u(\bar{x},t)$ of each tissue point $\bar{x}$ can be represented by its amplitude $a(\bar{x})$ and its phase $\varphi(\bar{x})$, as a complex number. The complex number representation, which we denote by $U_f(\bar{x})$ is defined as the phasor of the displacement at point $\bar{x}$ at frequency f.

$$u(\bar{x},t)=a(\bar{x})\sin(2\pi ft+\varphi(\bar{x}))\rightarrow U_f(\bar{x})=a(\bar{x})\exp(j\varphi(\bar{x})) \quad (2)$$

In some other embodiments of the elastography method, the excitation signal v(t) can be the sum of at least two sinusoids at different frequencies:

$$v(t)=\sum_i b_i\sin(2\pi f_i t+\theta_i) \quad (3)$$

At steady-state, the displacement of each point in the tissue u(t) is also a sum of sinusoids at the same frequencies as contained in the excitation:

$$u(\bar{x},t)=\sum_i a_i(\bar{x})\sin(2\pi f_i t+\varphi_i(\bar{x})) \quad (4)$$

and a phasor of displacement for every specified frequency $f_i$ is defined as:

$$U_{f_1}(\bar{x})=a_1(\bar{x})\exp(j\varphi_1(\bar{x})), U_{f_2}(\bar{x})=a_2(\bar{x})\exp(j\varphi_2(\bar{x})), \quad (5)$$

Displacement Estimation

Figure 11:
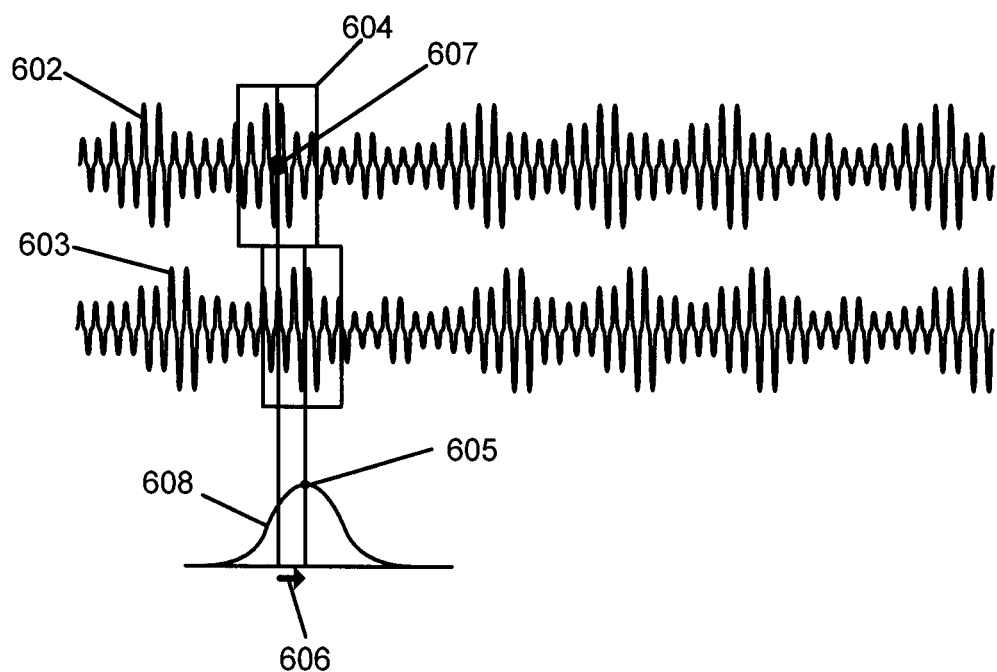
FIG. 11 is a diagram depicting a cross-correlation method for estimating displacements between two ultrasound RF-lines according to an embodiment of the invention.

Referring to FIG. 11, the described embodiments of the elastography method employ a process of estimating tissue displacement from radio frequency (RF) data 602 and 603 collected by the ultrasound machine at two different times.

Such tissue displacement estimation can be based on processes known in the art, such as those described by A Manduca, R Muthupillai, P J Rossman, J F Greenleaf, and R L Ehman in "Local wavelength estimation for magnetic resonance elastography" (Proceedings International Conference on Image Processing, 1996, Vol. 3, pp. 527-530.)

The two sets of RF data 602 and 603 are acquired at different times, between which the displacements are to be estimated. The RF data 602 and 603 are divided into blocks 604 and a search is carried out for blocks that match according to a similarity measure. Each block 604 represents a small volume of tissue located at a typical point $\bar{x}$ 607 in the tissue.

Figure 12:
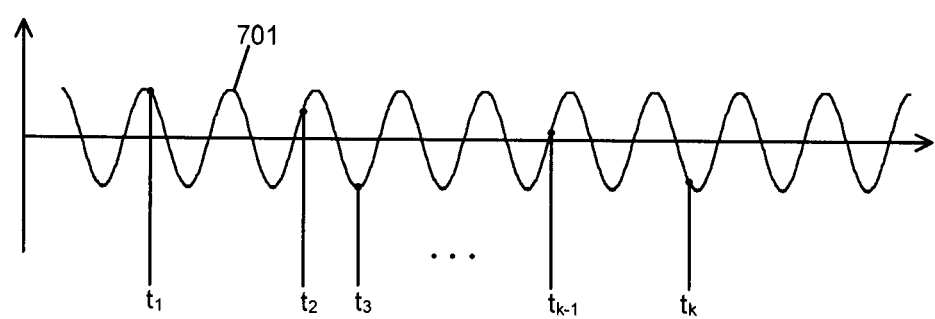
FIG. 12 is a diagram depicting a sampling of a sinusoidal signal at different time intervals according to an embodiment of the invention.

In one embodiment of the elastography method, a normalized correlation 608 is used as the similarity measure. A peak of the correlation 605 shows a match (high similarity) between the blocks and a dislocation 606 between the matching blocks is assumed to be the displacement of a typical point $\bar{x}$, 607. This displacement 701 is shown in FIG. 12 as a function of time for a sinusoidal excitation. The result is an estimate for the displacement $u(\bar{x},(t_k,t_{k+1}))$ of a small volume of tissue at $\bar{x}$, between discrete times $t_k$ and $t_{k+1}$.

In one implementation of the displacement tracking, all the displacements for point $\bar{x}$ are computed with respect to a given time $t_1$. This method is known as absolute displacement tracking, and yields, for different times $t_1, t_2, t_3, \ldots, t_K$, displacements $$u(\bar{x},(t_1,t_1)), u(\bar{x},(t_1,t_2)), u(\bar{x},(t_1,t_3)), \ldots, u(\bar{x},(t_1,t_K)). \tag{6}$$

In another implementation, the displacements are computed between data from consecutive acquisition times. This method is known as relative displacement tracking, and yields, for different times $t_1, t_2, t_3, \ldots, t_K$, displacements $$u(\bar{x},(t_1,t_2)), u(\bar{x},(t_2,t_3)), u(\bar{x},(t_3,t_4)), \ldots, u(\bar{x},(t_{K-1},t_K)). \tag{7}$$

The absolute displacements can be found by taking the cumulative sum of the relative displacements, and the relative displacements can be found by taking the difference of the absolute displacements.

Phasor Displacement Estimation

In order for the present embodiments of the elastography method to use the aforementioned displacement data to determine the mechanical properties of the tissue, the displacement, or phasors, must be phase-synchronized. A phasor displacement estimation step can be performed to find phase-synchronized phasors ("in-sync phasors") $U_{f_i}(\bar{x})$ for each point $\bar{x}$ 607 inside the tissue, at the excitation frequencies $f_i$ from the calculated displacements $u(\bar{x},(t_k,t_{k+1}))$. This can be computationally challenging because the process in which an ultrasound image of the tissue is acquired by an ultrasound machine is not an instantaneous process. Due to the limited propagation speed of sound in tissue (around 1540 m/s), the process of acquiring a single image could take from hundreds of microseconds to hundreds of milliseconds, depending on the depth of imaging, field of view, resolution, pulse sequence scheme, etc. Therefore an ultrasound image is not a true snapshot of tissue motion at a single instant in time. This means the sampling times for the motion of different points are not the same, but are spread throughout the time axis. A blind estimation of the phasors which does not take into account the inter-relationship of the times of sampling and the frequencies of excitation results in "out-of-sync" phasors. Out-of-sync phasors must be brought in-sync before they are used to estimate tissue elasticity.

As will be discussed below, the inter-relation between the times $t_k$ at which the displacements are sampled and the frequencies of excitation $f_i$ are used to calculate the phase-synchronized phasors for different spatial points in the tissue.

Calculating the Phasors

As shown in FIG. 12, the excitation has a single frequency f. In this embodiment, the measured displacement 701 of the point $\bar{x}$ 607 is close to a sinusoid at frequency f. Motion of the patient and physician's hand holding the probe, and the measurement noise, can also contribute to the measured displacement 701 of the point $\bar{x}$ 607. By estimating the phasors at the frequency of excitation f, the effect of these extraneous components are filtered. Assume that by the ultrasound acquisition process, the point 607 is imaged at times $t_1, t_2, \ldots, t_K$ as shown in FIG. 12.

In one embodiment of the elastography method, the ultrasound machine records the time-stamp of the acquisition for each RF-line it acquires. The times at which the point $\bar{x}$ was scanned, i.e. $t_1$ to $t_K$, are found from the time-stamps of the RF-lines which contain the point $\bar{x}$ by adding a fixed delay determined by the depth of $\bar{x}$ to account for the time it takes for the ultrasound pulse emitted by the ultrasound to reach the point $\bar{x}$, sample it, and then return back to the ultrasound probe.

The amplitude and phase of the displacement can be found by a least squares error fitting of a model to the estimated displacement data. For example, in the case of absolute displacement, the model is:

$$u(\bar{x}, (t, t_1)) = u(\bar{x}, t) - u(\bar{x}, t_1) \tag{8}$$
$$= a\sin(2\pi f(t - t_1) + \varphi) + c$$
$$= \alpha\sin(2\pi f(t - t_1)) + \beta\cos(2\pi f(t - t_1)) + c$$

where $a = \sqrt{\alpha^2 + \beta^2}$, $\varphi = \tan^{-1}(\beta/\alpha)$, and the constant c is needed to account for the fact that the displacements are all relative to the displacement of point $\bar{x}$ at time $t_1$:

$$c = -u(\bar{x}, t_1) \tag{9}$$

The amplitude and phase are found by solving the following system of equations by using a least-squares technique as is known in the art:

$$\begin{bmatrix} 1 & \sin(2\pi f(t_1 - t_1)) & \cos(2\pi f(t_1 - t_1)) \\ 1 & \sin(2\pi f(t_2 - t_1)) & \cos(2\pi f(t_2 - t_1)) \\ \vdots & \vdots & \vdots \\ 1 & \sin(2\pi f(t_K - t_1)) & \cos(2\pi f(t_K - t_1)) \end{bmatrix} \begin{bmatrix} c \\ \alpha \\ \beta \end{bmatrix} = \begin{bmatrix} u(\bar{x}, (t_1, t_1)) \\ u(\bar{x}, (t_1, t_2)) \\ \vdots \\ u(\bar{x}, (t_1, t_K)) \end{bmatrix} \tag{10}$$

Note that the phase is estimated relative to $t_1$, meaning that it is assumed that the phase is zero at $t_1$.

In another embodiment of the elastography method, the excitation contains multiple frequencies and the amplitudes and phases for each of the phasors at different frequencies can be found by:

$$u(\bar{x}, (t, t_1)) = c + \sum_i a_i \sin(2\pi f(t - t_1) + \varphi_i) \tag{11}$$
$$= c + \sum_i \alpha_i \sin(2\pi f(t - t_1)) + \beta_i \cos(2\pi f(t - t_1))$$

Writing this equation for different times obtains:

$$\begin{bmatrix} 1 & \sin(2\pi f_1(t_1-t_1)) & \cos(2\pi f_1(t_1-t_1)) & \ldots & \sin(2\pi f_N(t_1-t_1)) & \cos(2\pi f_N(t_1-t_1)) \\ 1 & \sin(2\pi f_1(t_2-t_1)) & \cos(2\pi f_1(t_2-t_1)) & \ldots & \sin(2\pi f_N(t_2-t_1)) & \cos(2\pi f_N(t_2-t_1)) \\ \vdots & \vdots & \vdots & \ddots & \vdots & \vdots \\ 1 & \sin(2\pi f_1(t_K-t_1)) & \cos(2\pi f_1(t_K-t_1)) & \ldots & \sin(2\pi f_N(t_K-t_1)) & \cos(2\pi f_N(t_K-t_1)) \end{bmatrix} \quad (12)$$

$$\begin{bmatrix} c \\ \alpha_1 \\ \beta_1 \\ \vdots \\ \alpha_N \\ \beta_N \end{bmatrix} = \begin{bmatrix} u(\bar{x},(t_1,t_1)) \\ u(\bar{x},(t_1,t_2)) \\ \vdots \\ u(\bar{x},(t_1,t_K)) \end{bmatrix}$$

$$a_i\sqrt{\alpha_i^2+\beta_i^2},\; \varphi_i=\tan^{-1}(\beta_i/\alpha_i)$$

Again the phases are all relative to $t_1$.

Figure 13:
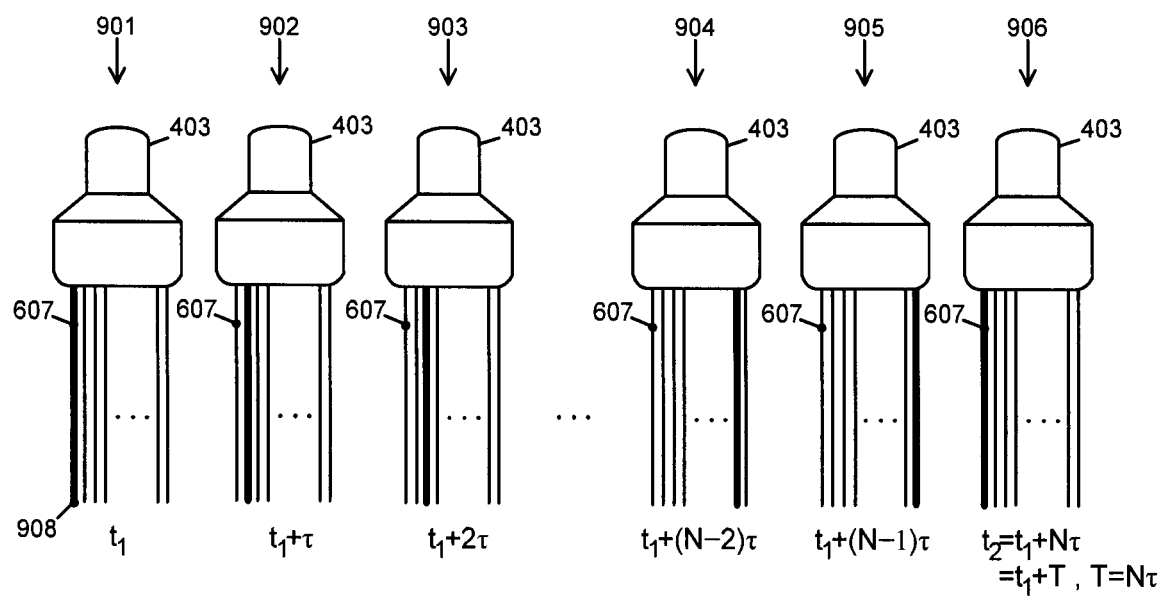
FIG. 13 is a diagram depicting sequential acquisition of RF-lines from a section of tissue with an ultrasound probe according to an embodiment of the invention.

FIG. 13 shows another embodiment in which the time points $t_1, \ldots, t_K$ at which the point $\bar{x}$ is scanned can be equally spaced in time:

$$t_2-t_1=t_3-t_2=\ldots=t_K-t_{K-1}=T \quad (13)$$

Many ultrasound machines scan the tissue line by line 901, 902, 903, 904 in this manner until the entire sector to be imaged is acquired 905, and repeat the same sequence 906 from the first line. In this case it is not necessary for the ultrasound machine to record the time-stamps for all the acquired RF-lines. It is sufficient to know the time interval T. The time interval T is determined by N, the number of lines in the sector, and the time for scanning each line $\tau$:

$$T=N\tau \quad (14)$$

The time for scanning each line $\tau$ should be enough for the ultrasound pulse to reach the deepest point 908 to be imaged, at depth d and return to the probe:

$$\tau > \frac{2d}{1540 \text{ m/s}} \quad (15)$$

In summary, the phasors can be determined from the matrix equations (10) or (12) by the knowledge of T.

In another embodiment of the elastography method, a Fourier-based method is used to compute the phasors, and either the time interval T between successive scans or the frequencies of excitation $f_i$ are adjusted such that:

1) The frequencies of excitation share a common period $f^{-1}$ (note that only in this case the steady-state excitation becomes periodic with period $f^{-1}$):

$$f_i=kf\; k\in\{1,2,3,\ldots\} \quad (16)$$

2) The time interval T is a rational fraction of the common period of excitation $f^{-1}$:

$$T=\frac{m}{n}f^{-1}\; m,n \in \{1,2,3,4,\ldots\} \quad (17)$$

In other words, from m periods of the excitation, n samples are taken.

For this purpose, either the excitation frequencies $f_i$ should be adjusted or the time interval should be adjusted using one or a combination of the following techniques:

changing the number of lines in the sector N;
changing the depth of imaging d, or point 908;
adding a wait time in the acquisition sequence;
synchronizing the acquisition of lines with an external pulse source with adjustable period. This pulse source can be the same source which generates the excitation.

Figure 14:
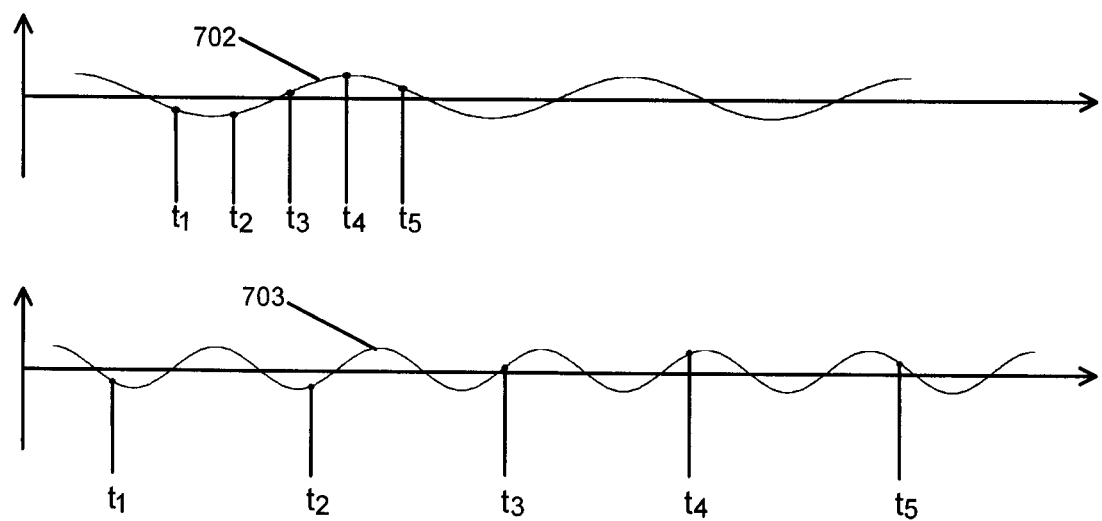
FIG. 14 is a diagram depicting sinusoidal signals sampled at two different sampling frequencies according to embodiments of the invention.

As mentioned above, such a relationship between T and $f_i$ makes it possible to use Fourier-based methods for computing the phasors. FIG. 14 shows an example 702 where T is one fifth of the excitation period. In this case, the phasors can also be computed by taking the discrete Fourier transform of the displacements. Another mathematically equivalent method to derive the phasors in this case is to multiply by $\exp(j2\pi ft)$ and sum over time:

$$U_f = \frac{1}{5}\sum_{i=1}^{5} \exp(j2\pi f \cdot iT)u(x,(t_1,t_i)) \quad (18)$$

FIG. 14 also shows an example 703 where T is six fifths of the excitation period. In this case, the motion is sampled at the exact same relative phase as the case in 702 but over different periods of the motion. However, the same techniques (discrete Fourier transform, and multiplication by $\exp(j2\pi ft)$) can be used to compute the phasor in this case as well. The fact that the phasors can be computed, even when the sampling rate is lower than the excitation frequency 703, is a consequence of the narrow bandwidth of the excitation in the frequency domain. This technique is known in the art as "bandpass sampling" and is explained by R Sinkus, J Lorenzen, D Schrader, M Lorenzen, M Dargatz, and D Holz in "High-resolution tensor MR elastography for breast tumour Detection" (Phys. Med. Biol. 45, 2000, pp. 1649-1664).

Phase Synchronizing the Phasors

Since the displacements for each point $\bar{x}$ 607 are derived relative to the displacements at time $t_1$ 901 of the point (as exemplarily shown in FIG. 13), the computed phase of the phasors is relative to $t_1$. The reference time is generally not the same for two different points $\bar{x}$ and $\bar{x}'$:

$$u(\bar{x},(t_1,t_k)) \rightarrow U_f(\bar{x})=a\exp(j\varphi) \text{ relative to } t_1$$

$$u(\bar{x}',(t'_1,t'_k)) \rightarrow U_f(\bar{x}')=a'\exp(j\varphi') \text{ relative to } t'_1; \quad (19)$$

Therefore the phase difference $\varphi-\varphi'$ does not represent the actual phase difference in the motion of the said two points.

It also includes the phase difference caused by the difference in reference times $t_1-t'_1$. The phasors can be brought in-sync (phase synchronized) by compensating for this extraneous phase difference:

$$u(\bar{x}',(t'_1,t'_k)) \rightarrow U_{f,in-phase}(\bar{x}')=a'\exp(j\varphi')\exp(j2\pi f(t_1-t'_1)) \text{ relative to } t_1 \quad (20)$$

In the embodiments of the elastography method where a time-stamp is recorded for each RF-line acquired by the ultrasound machine, the time-stamps are used to calculate the differences in reference times and bring the phasors in-sync using the above equation.

Figure 15:
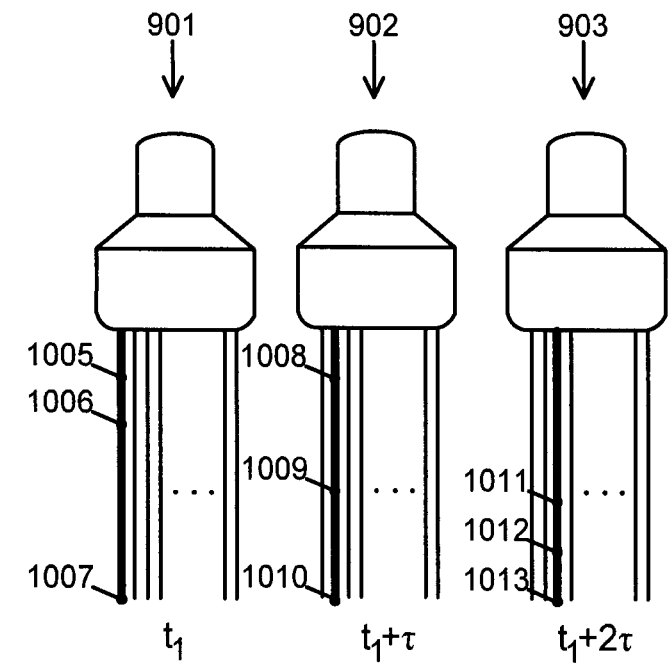
FIG. 15 is a diagram depicting the timeline of acquisition of data from different points in a section of tissue when the tissue is imaged by sequential acquisition of RF-lines from said section according to an embodiment of the invention.
Figure 15:
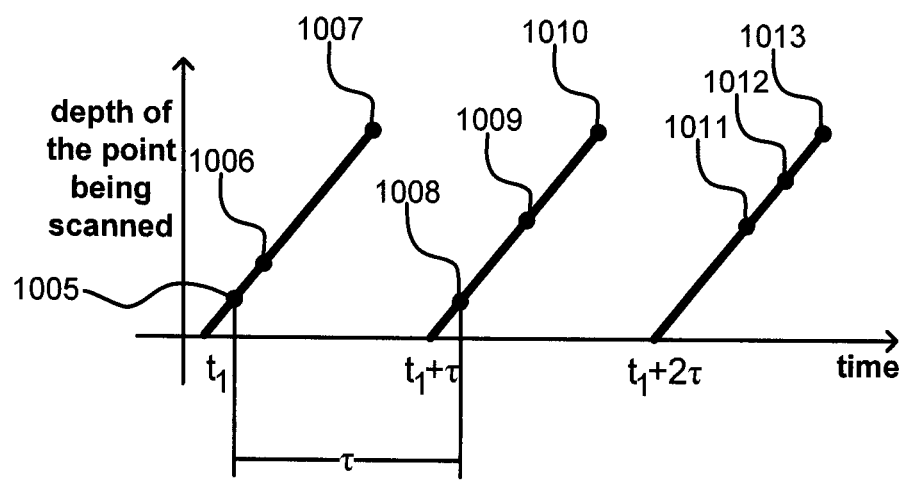

In the embodiments of the elastography method where the image is acquired line by line 901, 902, 903 and the delay between the acquisition of one line and the next is constant $\tau$, as shown in FIGS. 13 and 15, it is not necessary to know the absolute time-stamps of the RF-lines to perform the phase compensation.

As shown in FIG. 15, a time-line graph of acquisition can be plotted from which the delay between the acquisitions of any two points can be calculated. For the purpose of explanation, nine points have been marked 1005 to 1013 both on the scan-line sequence and time-line graph. For instance for two points $\bar{x}$ 1005 and $\bar{x}'$ 1008 which are at the same depth on two consecutive lines, the time delay is equal to $\tau$ and the corresponding phasors for these two said points can be brought in-sync by:

$$u(\bar{x}',(t'_1,t'_k)) \rightarrow U_{f,in-phase}(\bar{x}')=a'\exp(j\varphi')\exp(j2\pi f\tau) \quad (21)$$

Under some special circumstances, it is possible that the phase difference between two points becomes zero, in other words, the points are already in-sync and there is no need for phase compensation between them. For this to happen, we have:

$$\exp(j2\pi f(t_1-t'_1))=1$$

$$f(t_1-t'_1)=m \quad m \in \{0,1,2,3,\ldots\}$$

$$t_1-t'_1=mf^{-1} \quad m \in \{0,1,2,3,\ldots\} \quad (22)$$

To utilize this property, the time interval between scanning of consecutive lines $\tau$ and the frequencies of excitation $f_i$ are adjusted such that:

1) the frequencies of excitation share a common period $f^{-1}$;
2) the time interval $\tau$ is an integer multiple of the common period of excitation $f^{-1}$.

Estimating Two Components of the Displacement

Methods of acquiring RF-lines at different angles using conventional beam-steering in order to compute two components of the displacement (axial and lateral) are known in the art, and for example are discussed by R Zahiri-Azar, A Baghani, S E Salcudean, and R Rohling in "2D High Frame Rate Dynamic Elastography Using Delay Compensated and Angularly Compounded Motion Vectors: Preliminary Results" (IEEE trans. Ultrason., Ferroelect., Freq. contr, Vol 57, No 11, November 2010, pp. 2421-2436).

In some embodiments of the elastography method, RF-lines are acquired at least at two different angles and the calculated phasors of displacements along the two or more directions are combined to calculate the axial and lateral displacements.

Calculating Absolute Elasticity and Viscosity from Phasor Displacements

Mechanical vibrations in the range of 2 Hz to 1000 Hz generated and transferred to the tissue by the excitation sources propagate through the tissue as shear waves. The governing equation for the propagation of these waves assuming a purely elastic model is:

$$\rho \frac{\partial^2}{\partial t^2} u(x,y,z,t) = \mu \left( \frac{\partial^2}{\partial x^2} + \frac{\partial^2}{\partial y^2} + \frac{\partial^2}{\partial z^2} \right) u(x,y,z,t) \quad (23)$$

where $\rho$ is the density and $\mu$ is the shear modulus and the coordinates of the point $\bar{x}$ are denoted by (x, y, z). Since biological tissue is nearly incompressible, its elastic modulus E is equal to $3\mu$ and therefore measurements of elasticity and shear modulus are equivalent. For a steady-state excitation at a frequency f, the equation governing the phasor of the displacement at the frequency f becomes, $$-\rho(2\pi f)^2 U_f(x,y,z) = \frac{E}{3} \left( \frac{\partial^2}{\partial x^2} + \frac{\partial^2}{\partial y^2} + \frac{\partial^2}{\partial z^2} \right) U_f(x,y,z) \quad (24)$$

Biological tissue is not purely elastic in nature. One way to model visco-elastic nature of tissue is to consider $\mu$ to be a complex number, which is a function of frequency, $$\mu=\mu(f)=\mu_{RE}(f)+j\mu_{IM}(f) \quad (25)$$

where $\mu_{RE}$ is associated with shear elasticity and $\mu_{IM}$ is related to shear viscosity.

Methods for calculating absolute values of elasticity and viscosity from the phasors are known in the art and can be implemented in the elastography method of the present embodiments to compute any of, but not limited, to: elasticity, shear modulus, shear wave speed and viscosity.

For example, direct inversion of the wave equation method, as described by R Sinkus, J Lorenzen, D Schrader, M Lorenzen, M Dargatz, and D Holz in "High-resolution tensor MR elastography for breast tumour detection" (Phys. Med. Biol. 45, 2000, pp. 1649-1664), can be used to find the elasticity by inverting the wave equation (24), $$E = -3\rho(2\pi f)^2 \frac{U_f}{\left( \frac{\partial^2}{\partial x^2} + \frac{\partial^2}{\partial y^2} + \frac{\partial^2}{\partial z^2} \right) U_f} \quad (26)$$

$U_f$ can be filtered, and for instance can be low pass filtered to remove noise or high pass filtered to remove the zero-frequency component or both before being used in equation (26).

In local frequency estimation (LFE) the phasors are directionally filtered and passed through a set of filter banks, in a manner known in the art such as that described by A Manduca, R Muthupillai, P J Rossman, J F Greenleaf, and R L Ehman in "Local wavelength estimation for magnetic resonance elastography" (Proceedings International Conference on Image Processing, 1996, Vol. 3, pp. 527-530). The ratio of the outputs of each pair of the filters gives an estimate for the local frequency of the signal, provided that the local frequency is within the bandwidth of the filter pairs used. A weighted sum of the estimates is used as the measure of the local frequency. The local (spatial angular) frequency, k, is related to elasticity by, $$E = -3\rho(2\pi f)^2 \frac{1}{-k^2(x,y,z)} \quad (27)$$

Again appropriate filtering might be applied to $U_f$ before being used in the filter banks, as part of the algorithm.

In travelling wave expansion (TWE) a sum of travelling waves in different directions with different amplitudes and phases is used as a model with the local (spatial angular) frequency as the model parameter. The model is then fitted locally to the phasor by finding the best local frequency. The elasticity can be computed from the estimated local (spatial angular) frequency as in (27) in a manner known in the art.

In finite element method (FEM) a forward model is fitted iteratively to the phasors, each time adjusting the presumed distribution of the mechanical properties until the actual absolute values of the mechanical properties are found; an exemplary approach is described by H Eskandari, S E Salcudean, R Rohling and J Ohayon in "Viscoelastic Characterization of Soft Tissue from Dynamic Finite Element Models" (Physics in Medicine and Biology, Vol. 53, No. 22, pp. 6569-6590, November 2008).

Volumetric Imaging for Absolute Elastography

As described by equation (24), an accurate estimate of elasticity E requires the measurement of the displacement phasor over a 3D volume. In other words, the vibrations in reality propagate in the 3D volume of the biological tissue. To measure the spatial frequency of such vibrations, it is necessary to measure them over a 3D volume. Therefore, in the present embodiments of the elastography method, ultrasound data are collected from a 3D volume of the tissue (volumetric imaging) using a single 3D ultrasound probe.

Generally speaking, a suitable 3D ultrasound probe emits sound waves into a 3D volume defining the tissue to be imaged. The received data from the reflected sound waves create a volumetric dataset (often abbreviated as "volume") of the anatomy, unlike a 2D ultrasound probe which creates images of a cross-sectional plane. Real-time 3D ultrasound imaging can be implemented by at least the following two known methods:

1) mechanical sweeping: A specialized 3D probe is constructed by combining a 2D probe with a motorized mechanism for rapidly moving the 2D probe so that the 2D image sweeps repeatedly through a volume of interest. Repeated sweeping is usually implemented in an oscillating manner where each oscillation produces a 3D volume. The spatial relationship between the set of 2D images from each oscillation is known because the probe motion is controlled and the images are reconstructed into a 3D Cartesian volume. This device is referred to hereafter as a mechanical 3D probe;

2) multidimensional arrays: A specialized probe is created without a motorized mechanism, but instead uses a two dimensional array of transducers to scan over a 3D volume of interest. The speed of volume acquisition is typically higher than mechanical probes but the complexity of the probe increases and image quality can be inferior. This probe is known as a multidimensional probe.

The 3D ultrasound probe used in the present embodiments of the elastography method can be a mechanical 3D probe or a multi-dimensional 3D probe as known in the art, or as described below.

An example of a suitable known mechanical 3D probe is the RAB2-5 H46701M for the Voluson 730 ultrasound machine by General Electric Corporation (GE Healthcare, Chalfont St. Giles, United Kingdom). An example of a suitable known multidimensional probe is the X7-2 for the Philips iU22 ultrasound machine (Philips Healthcare, Andover, Mass., USA).

Figure 16:
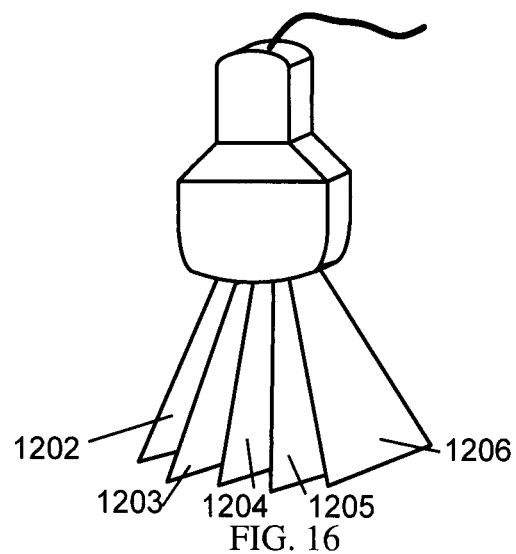
FIG. 16 is a diagram depicting a motorized external 3D probe according to an embodiment of the invention.
Figure 17:
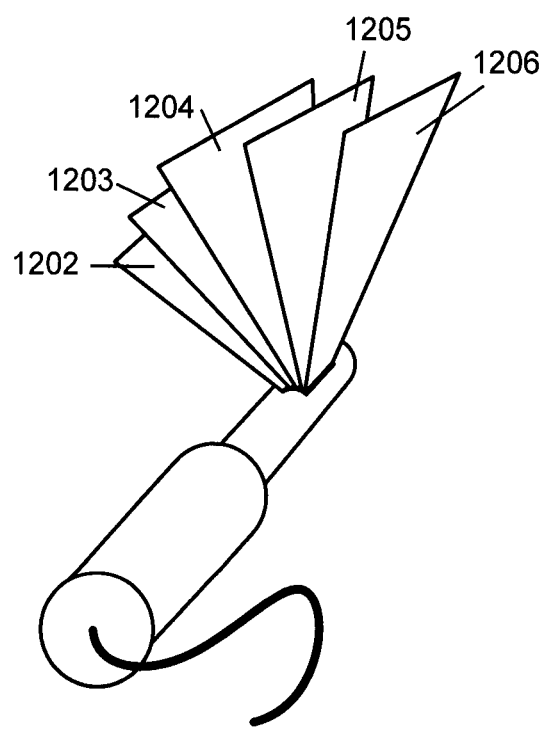
FIG. 17 is a diagram depicting a motorized endo-cavity 3D probe according to an embodiment of the invention.
Figure 18:
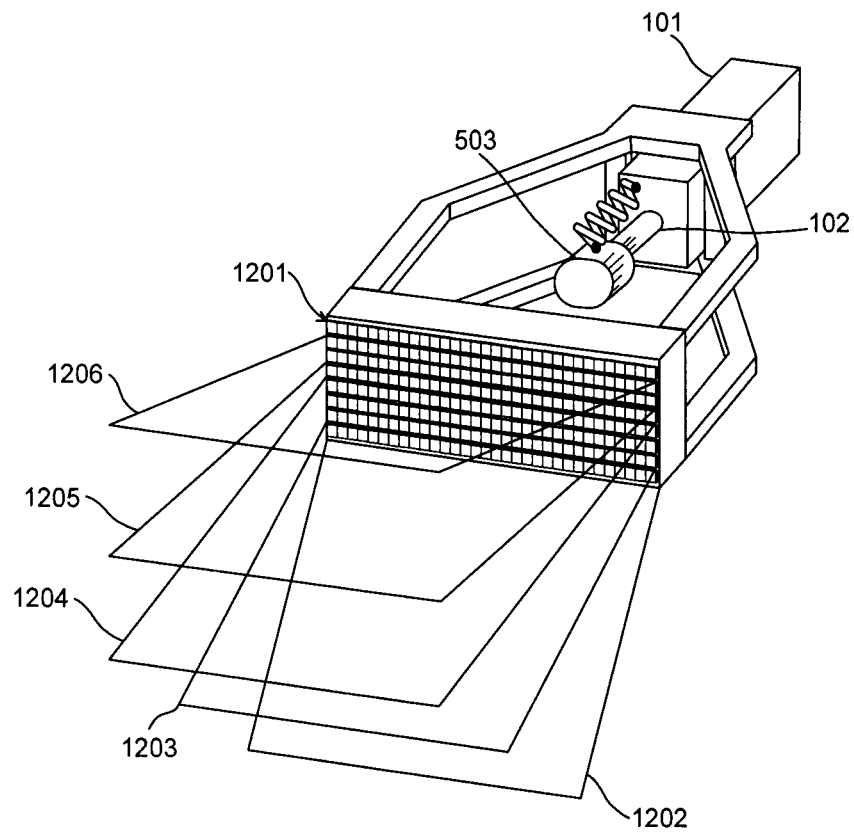
FIG. 18 is a diagram depicting a matrix array 3D probe with a vibration source integrated according to an embodiment of the invention, wherein the probe acquires 3D data one plane at a time.
Figure 19:
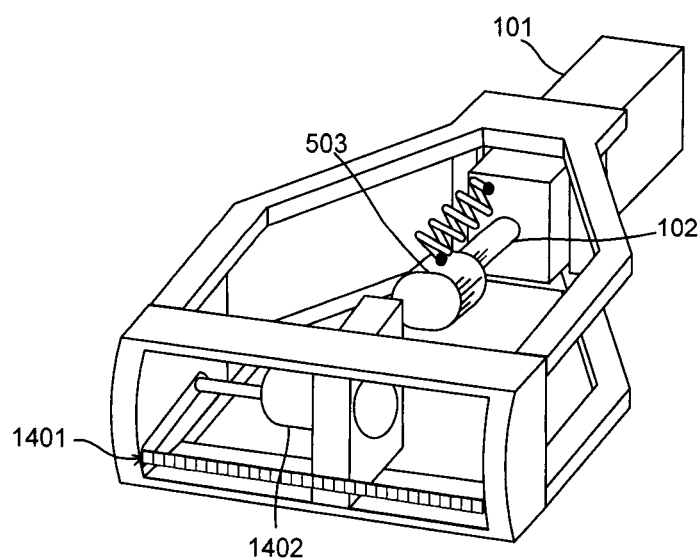
FIG. 19 is a diagram depicting a motorized 3D probe with a vibration source integrated according to an embodiment of the invention.
Figure 20:
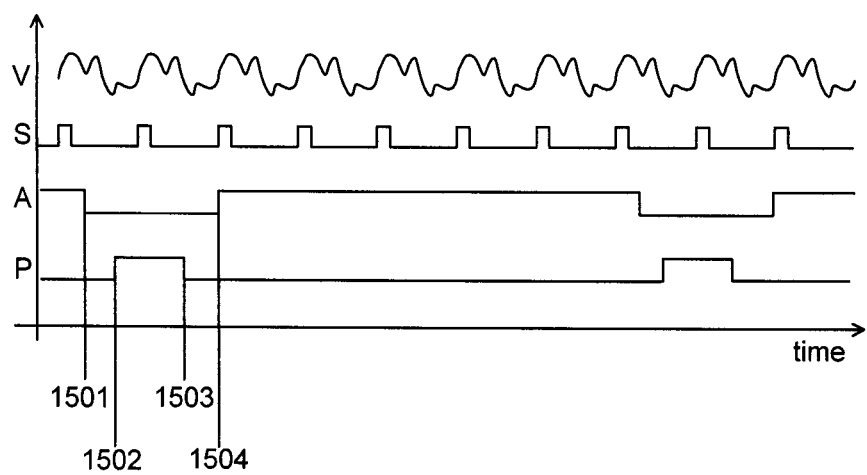
FIG. 20 is a timing diagram depicting the correlation between excitation and sync signals, and image acquisition and plane switch signals
Figure 21:
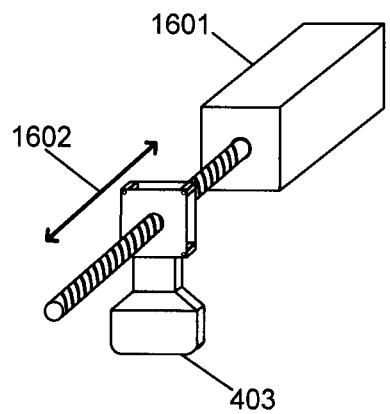
FIG. 21 is a perspective view of an external motion stage used with an external 2D probe to generate 3D data according to an embodiment of the invention.
Figure 22:
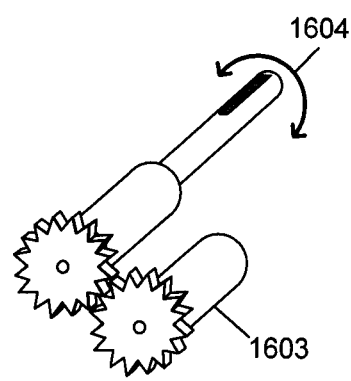
FIG. 22 is a perspective view of an external motion stage used with an endo-cavity 2D probe to generate 3D data according to an embodiment of the invention.

Mechanical and multi-dimensional 3D probes according to different embodiments are shown in FIGS. 16 to 22. An external 3D motorized linear array ultrasound probe as shown in FIG. 16. An endo-cavity 3D motorized ultrasound probe is shown schematically in FIG. 17 and can acquire 3D volume images from the imaging of multiple planes. A matrix array 3D ultrasound probe is shown in FIG. 18 having the vibration source integrated into the probe. A motorized 3D ultrasound probe is shown in FIG. 19 also with the vibration source integrated according to an embodiment of the invention. A pair of mechanical 3D ultrasound probes using a 2D probe with an external motion stage are shown in FIGS. 21 and 22. Regardless of which 3D ultrasound probe is used in the present embodiments of the elastography method, the volumetric data is acquired as follows:

(a) a volume of the tissue is divided into multiple planes.
(b) each plane is imaged over a time interval such that each point in the plane is scanned multiple times; and
(c) the process is repeated for all the planes.

As noted above, the 3D ultrasound probe takes obtains a thin volume of the tissue which comprises a desired cross-sectional plane and at least two adjacent planes. For example, in FIGS. 16, 17 and 18, the thin volume being imaged is the convex hull of all planes, the desired cross-sectional plane is shown as 1204, and adjacent planes are shown as 1203, 1202 and 1205, 1206, which are all adjacent to the cross-sectional plane 1204 with planes 1203 and 1205 being immediately adjacent to the cross-sectional plane 1204. In some situations, it is desirable to adjust the spacing between adjacent planes to more accurately capture the change in phasors in the elevational direction.

The 3D ultrasound probe as shown in FIG. 18 comprises a matrix array 1201 of transducers which is used to steer the ultrasound imaging plane and acquire multiple planes 1202, 1203, 1204, 1205, 1206 to form a volume. In this probe, the imaging plane is switched electronically, and therefore the acquisition can be performed faster, and higher overall frame rates can be achieved, compared to other types of probes. The vibration mechanism used in the embodiment of FIG. 18 is a mass 503 which is substantially the same as that shown in FIG. 10. This ultrasound probe with a matrix array of transducers can use synthetic aperture beam forming to reconstruct the RF-lines covering the 3D volume. An example of such a probe is described by Jørgen Arendt Jensen, Svetoslav Ivanov Nikolov, Kim Løkke Gammelmark, and Morten Høgholm Pedersen in "Synthetic aperture ultrasound imaging" (Ultrasonics 44, 2006, pp. e5-e15). Alternatively, this ultrasound probe with a matrix array of transducers can use micro-beam forming to reconstruct the RF lines covering the 3D volume. An example of such a probe is described by Christopher Hall in "4-Dimensional Ultrasonic Imaging" (Advances in Health care Technology Care Shaping the Future of Medical, Philips Research Book Series, 2006, Volume 6, No. 2, pp. 99-116).

The ultrasound probe shown in FIG. 19 includes a linear transducer array 1401 and a motor 1402 for sweeping the array over a sector of angles. In this probe, the motion of the probe from one plane to the next creates a new time-delay in the acquisition process of the ultrasound RF-lines. This is the time required by the mechanical motion inside the probe to settle. If the time-stamps for the acquired RF-lines on different planes are available, this information can be used as in equation (20) to bring the phasors in-sync. The vibration mechanism is a mass 503, which is substantially the same as that shown in FIG. 10. FIG. 20 shows the correlation between the excitation and sync signals, the image acquisition and plane switch signals according to an embodiment of the invention. As shown in FIG. 20, the frequencies of excitation (V) share a common period $f^{-1}$, and a sync signal (S) is generated with the same period $f^{-1}$. The sync signal S is used to synchronize the start 1504 of the acquisition on each imaging plane with the vibration source. FIG. 20 shows one example timing diagram used for this purpose. In this diagram the sync signal S is synchronous with the vibration signal V. The acquisition of RF-lines is controlled by the acquisition signal A, and P is the plane switch signal, for instance going to the controller of the motor 1402. After the data has been acquired for one plane 1501, the motor is ordered to move to a new plane 1502. After the motor has settled in the new position 1503 the system listens for the next rising edge on the sync signal S to start the acquisition of the next plane 1504.

Alternatively, a mechanical 3D probe comprising a 2D probe with an external motion stage can be used to image a 3D volume, For example, an external motion stage 1601 used with an external 2D probe is shown in FIG. 21 to generate 3D data according to one alternative embodiment, while FIG. 22 shows a mechanical 3D probe comprising a an external motion stage 1603 used with an endo-cavity 2D probe to generate 3D data according to another embodiment. The external motion stages 1601, 1603 move a 2D probe 403 fixed to the said motion stage, to acquire multiple planes, labeled as 1602 in FIGS. 21 and 1604 in FIG. 22. In these embodiments, the timing of the acquisition for the different planes can either be recorded by time-stamps or be synchronized with the excitation, in order to bring the displacements phasors of different planes in-sync.

Unlike the regular spacing of the displacement measurements in MRE that fall along equally-spaced Cartesian locations within planes that are parallel, displacement measurements with ultrasound are not typically at equally-spaced Cartesian locations. This can be seen by the non-parallel spacing of the planes in FIGS. 16 and 17. In the case of such ultrasound data there is therefore a need to accommodate the particular spacing of the measurements so that the calculations of the absolute elasticity and viscosity are performed in Cartesian coordinates, as shown in equations (23), (24), (26), and (27). Given that the phase-synchronization of the phasors incorporates the positions of the measurements, then the phase-synchronization steps should incorporate the actual spatial locations of the ultrasound beams and planes.

Performing the Computations in Real-Time

Figure 23:
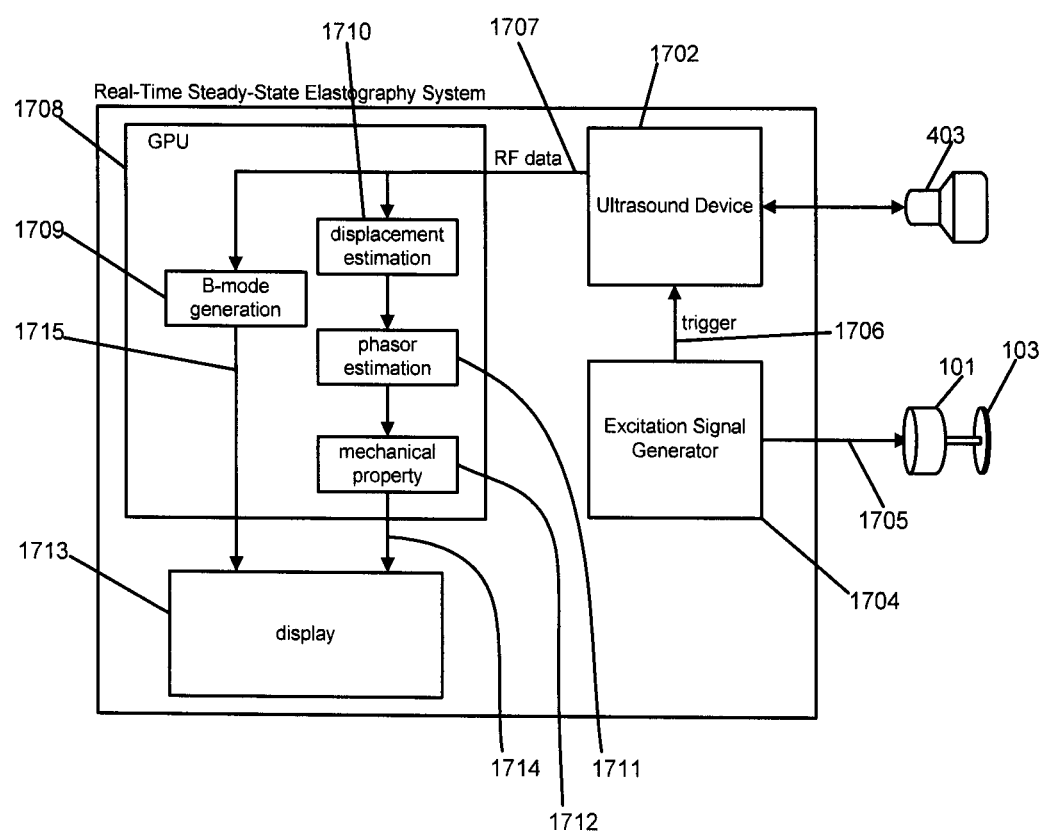
FIG. 23 is a block diagram depicting an ultrasound elastography system for performing real time elastography of a subject according to an embodiment of the invention.

Referring now to FIG. 23, an elastography system is provided which performs the elastography method described above. This system comprises an ultrasound machine 1702 coupled to the ultrasound probe 403, an excitation signal generator 1704 (otherwise known as a waveform generator) coupled to the vibration source 101, circuitry communicative with the ultrasound machine and comprising a processing unit (GPU) 1708 with a memory having programmed thereon steps and instructions embodying the elastography method that are executable by the GPU 1708, and a display 1713 for displaying the imaged tissue and the mechanical properties of the tissue as determined by the elastography method.

The GPU 1708 can have parallel processing capability, which can be utilized to reduce the computational time for estimating the mechanical properties relative to the acquisition time of the RF-data. The ultrasound machine 1702 can acquire RF-data 1707 from the probe 403 and send the RF-data 1707 to the GPU 1708. The GPU 1708 has a B-mode generation software module 1709 that generates and sends a B-mode image 1715 to the display 1713 in a manner that is well known in the art. The GPU 1708 also has a displacement estimation module 1710 that computes tissue displacements in at least one axis, a phasor generation software module 1711 and a software module to compute the mechanical properties of tissue 1712. In one implementation, the GPU 1708 sends images of the mechanical properties to the display 1713, which are overlaid on the B-mode images and shown to the user. The waveform generator 1704 creates a signal 1705 for the vibration source 101 and also a trigger signal 1706 for the ultrasound machine 1702.

Parallel processing GPUs can incorporate hundreds of processing units. Such GPUs are capable of executing thousands of threads (sequential programs) simultaneously. The computations defined in the elastography method are highly parallelizable and thus suitable for execution by a parallel processing GPU. The CUDA™ library provided by NVIDIA® can be used to compile the multithreaded programs for the GPU, following the approaches specified in NVIDIA Corporation's "NVIDIA CUDA C Programming Guide" and "OpenCL Programming for the CUDA Architecture". A detailed example of how to use the CUDA™ library for image filtering is provided by Victor Podlozhnyuk in "Image convolution with cuda" (Technical report, NVIDIA Corporation, 2007).

Figure 24:
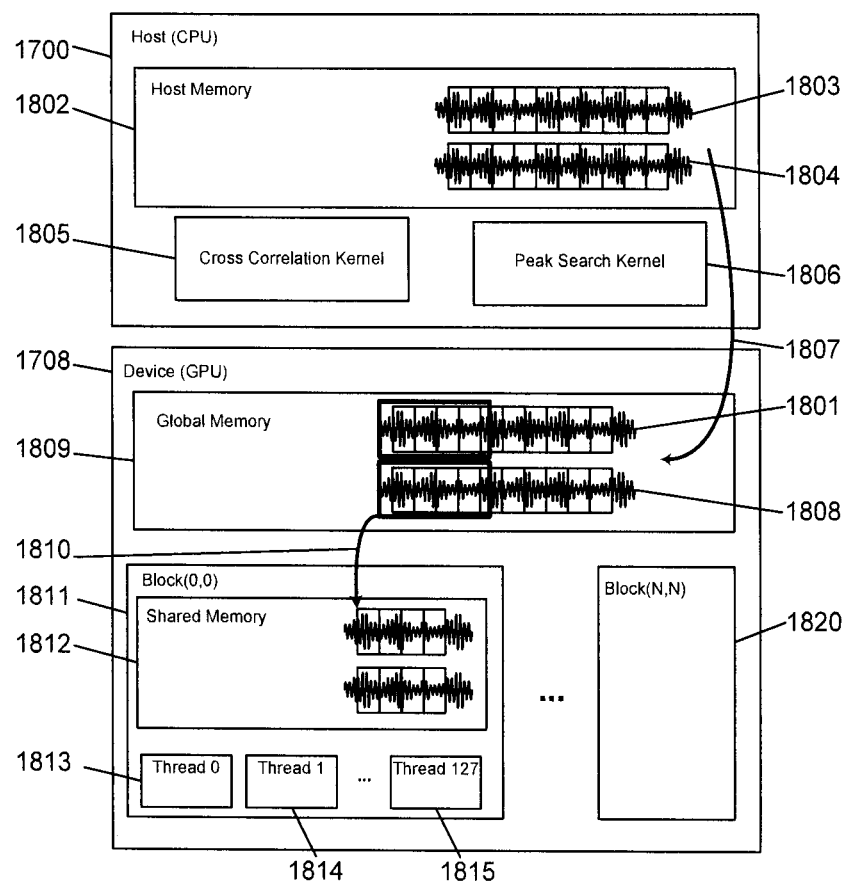
FIG. 24 is a block diagram depicting a correlation based motion estimation algorithm implemented by a GPU in the elastography system.

FIG. 24 is a block diagram showing another embodiment of an elastography system performing the elastography method, which executes a correlation based motion estimation algorithm to perform the elastography method. In this system, each step of computing the cross correlation for the displacement estimation between each corresponding two RF-lines 1803 and 1804 is carried out in a separate thread. Two kernels 1805 and 1806 run on a host processor (CPU) 1700. The cross correlation kernel 1805 copies 1807 the RF-lines 1803 and 1804 from the CPU memory 1802 to a global memory 1809 of the GPU 1708. The data is split into windows. The data needed for finding the displacements of a number of adjacent windows, for instance four windows, from the two RF-lines 1801 and 1808 are then copied 1810 to a GPU block 1811 in the GPU 1708 and the same procedure is repeated for other groups of four windows to other blocks such that the task of finding cross correlation is distributed between the blocks 1811 similarly 1820 of the GPU 1708. In each block, 128 threads 1813, 1814, 1815 compute the cross correlations for different amount of shifts for each window. All the threads run in parallel and are synchronized at the point when the cross correlations for all the blocks are computed. The cross correlations are written to the global memory 1809.

The second kernel 1806, otherwise known as the peak search kernel, distributes the cross correlations between the blocks and finds the peak of the cross-correlation for each window, synchronizes at the end to ensure all the peaks have been found, and writes back to the global memory 1809 on the GPU 1708. The final displacements are then transferred back to the CPU memory 1802.

In another embodiment, the CULA™ library is used to perform fast multi-threaded matrix algebra. The CULA™ library is used to calculate the phasors from time displacement by solving equation (12). The time displacements for different points (right hand side of equation 12) are grouped together in one matrix so that a single call to the CULA™ solver can provide the phasors for all the points at the same time. Preferably, the phasors for different points are brought in-sync by a kernel. The kernel executes the phase compensation for each point in a separate thread.

Further, the CUFFT™ provided by NVIDIA® can be used to perform the Fourier transform required for LFE filtering. Alternatively, the CULA™ library can be used to solve matrix equations of FEM.

Some of the aforementioned computations can also be performed on a field-programmable gate array (FPGA) in an efficient way, or on a digital signal processor (DSP).

Acquisition of a Thin Volume in Real-Time

It is of interest to acquire a 2D image that depicts the mechanical properties of tissue, for instance elasticity, along a cross-sectional plane of the tissue in a real-time or high frame-rate of at least one frame per five seconds and preferably closer to or at one frame per $30^{th}$ of a second. Radiologists, ultrasound technicians, physicians, nurses and other users of ultrasound machines often use real-time 2D imaging for locating malignancies and for diagnosis. The present embodiments enable real time computational processing of the elastography method and thus makes it possible for users to observe the changes in the displayed images as they slowly move the probe.

In the described embodiments of the elastography method, the data is acquired from a desired cross-sectional plane of the tissue and at least two other planes adjacent to the desired plane. Such a volume of data is called a thin volume, because the extents of the volume in the desired plane are larger than the extent of the volume in the third (out-of-plane) dimension by a factor of at least 3. Thin volumes can be acquired in real-time more easily than larger volumes. The data is then used to estimate mechanical properties such as elasticity on said desired cross-sectional plane and the result shown as a 2D image to the user.

The use of measurements of the displacement phasors over a volume is beneficial because it allows the measurement of the spatial wavelength to be performed in all three spatial directions. The speed of the imaging process is proportional to the size of the volume. A smaller volume is beneficial because it achieves faster imaging rates. The minimum number of data points in any of the spatial directions required to calculate the spatial wavelength is three, as three data points allow the second spatial derivative to be calculated, which can be used for measuring the spatial wavelength. As a result, with thin volume and synchronized acquisition, and efficient phase correction, embodiments of the invention can realize real-time or high-frame-rate ultrasound elastography.

Figure 25:
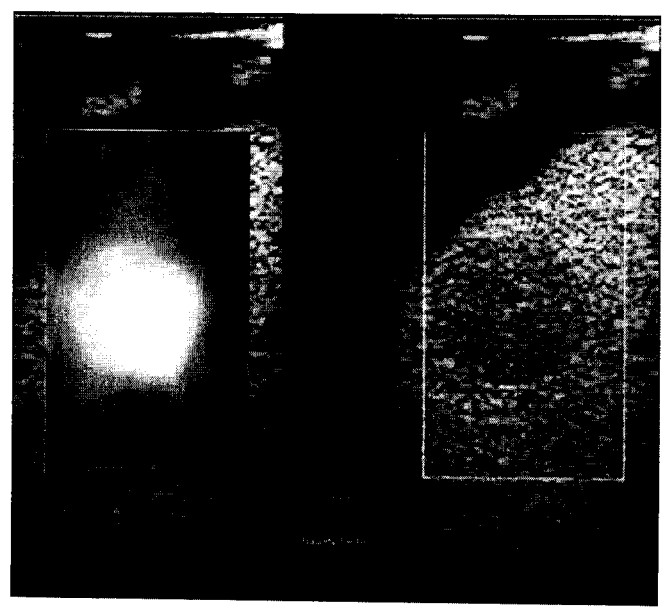
FIG. 25 depicts an exemplary absolute elasticity image obtained by the elastography system.

FIG. 25 shows an example absolute elasticity image collected by an embodiment of the elastography system. The system was used to image a tissue phantom with the following imaging parameters: the time for scanning each line, τ, was equal to 125 microseconds which enabled an imaging depth of 80 mm. The number of lines in the sector N was equal to 32, with a line spacing of 1.2 mm. The resulting sector width was equal to 38.4 mm. Each plane was scanned 30 times. The time of acquisition for the plane was 30×32× 125 µs=120 ms. Seven planes were acquired with a spacing of 1.2 mm between adjacent planes, which required 7×120 ms=0.84 seconds. A motorized 3D probe was used (FIG. 19) which required 20 ms for moving the crystals from one plane to the next. The total acquisition time for each frame was therefore: 0.84 s+7×20 ms=0.98 second. The processing of the data did not cause a significant overhead on the acquisition time (less than 100 ms). The size of the thin volume in this example was 38.4 mm by 80 mm in the plane of interest, and 8.4 mm for the third (out-of-plane) dimension. The displacement and phasors were estimated as the data became available. The plane of interest was the central plane and the elasticity in the central plane of the acquired seven planes was estimated using the LFE method and shown in real-time. The resulting frame rate was one frame per second. FIG. 25 shows one frame of the resulting elastogram overlaid on the B-mode image and the B-mode image side-by-side. The imaging of the absolute value of tissue elasticity in a commonly used, reasonable region of interest of approximately 80 mm by 40 mm can thus be accomplished in less than one second. This means that the elastography system can display absolute elasticity images at a refresh rate of more than 1 frame per second.

Other image sizes used in standard ultrasound examinations involve depths up to 200 mm and line density of 64 lines per sector. Assuming seven planes of acquisition as before the elasticity image refresh rate will be approximately one new frame for every 5 seconds.

There will always be a tradeoff between the number of planes used in the thin volume and the resulting imaging frame rate. The accuracy of determining the change in phasors in the elevational direction depends on the number of points used. Three planes is the minimum and will produce the highest elasticity imaging frame rate. More planes will provide additional measured phasor locations and therefore will increase the elasticity image accuracy. We have found that with standard elasticity phantoms, seven planes provide a good compromise between image accuracy and imaging frame rate.

While specific embodiments have been described and illustrated, such embodiments should be considered illustrative only and not as limiting the invention.

The invention claimed is:

1. An elastography method for imaging at least one mechanical property of a tissue in a desired cross-sectional plane of said tissue, the method comprising:
   applying a steady-state vibration to said tissue to generate time varying tissue displacements in said tissue;
   ultrasound imaging a thin volume of said tissue over a time period by acquiring a set of image data representing the thin volume over said time period, the thin volume including said desired cross-sectional plane and at least two planes adjacent to said desired cross-sectional plane;
   for each of a plurality of spatial points in the thin volume, computationally estimating a time varying estimated displacement of the tissue at the point over the time period using the set of image data, wherein at least one of the spatial points is located on each of the cross-sectional plane and the adjacent planes; and
   adjusting the time varying estimated displacements to compensate for phase differences among the estimated displacements for different ones of the spatial points, the phase differences resulting from differences in times at which the ultrasound imaging images the different ones of the spatial points, the adjusting causing phases of the plurality of time varying estimated displacements to be synchronized relative to a common reference time; and
   computationally determining said at least one mechanical property of said tissue on said desired cross-sectional plane by using said plurality of phase-synchronized estimated displacements;
   wherein the number of adjacent planes is selected such that said at least one mechanical property of said tissue can be computationally determined within a real time refresh rate.

2. A method as claimed in claim 1 wherein real time refresh rate is at least one new frame per five seconds.

3. A method according to claim 1, wherein said thin volume is imaged by a single three dimensional (3D) ultrasound probe.

4. A method according to claim 1, wherein the estimated displacement is in a direction of propagation of ultrasound of the ultrasound imaging.

5. A method according to claim 1, wherein said at least one mechanical property includes any one or more properties selected from absolute elasticity, absolute shear modulus, absolute shear wave speed, and absolute viscosity.

6. A method according to claim 4, wherein said at least one mechanical property is calculated from said plurality of estimated displacements by using any one or a combination of finite element method, local frequency estimators, travelling wave expansion and direct inversion.

7. A method according to claim 1, wherein said image data comprises a plurality of RF-lines, a time of acquisition for each of the plurality of RF-lines is recorded, and the method comprises:
computing a delay of each of the RF: lines with respect to a period of the steady-state vibration based on the time of acquisition.

8. A method according to claim 1, wherein said image data comprises a plurality of RF-lines which are acquired line-by-line with equal time intervals, and the method comprises:
computing a delay of each RF-line with respect to a period of the steady-state vibration based on the time intervals.

9. A method according to claim 8, wherein the steady-state vibration is synchronized with the acquisition of the RF-lines, so that each RF-line is acquired at a constant delay with respect to the period of vibration.

10. A method according to claim 1, wherein the acquisition of image data of each of the planes in the thin volume is synchronized with a period of the steady-state vibration.

11. A method according to claim 1, wherein the steady-state vibration is a harmonic sinusoidal excitation.

12. A method according to claim 1, wherein the steady-state vibration is a sum of multiple sinusoidal excitations with different frequencies, and different amplitudes and phases.

13. A method according to claim 12, wherein the ultrasound imaging comprises acquiring a plurality of RF-lines, the frequencies of excitation share a common period and the acquisition of each of the plurality of RF-lines is synchronized with the common period, a rational fraction or an integer multiple of the common period.

14. A method according to claim 1, wherein said thin volume has extents of the volume in the desired plane that are larger than the extent of the volume in a third dimension perpendicular to the desired plane by a factor of at least 3.

15. An elastography system for imaging at least one mechanical property of a tissue in a desired cross-sectional plane of said tissue, comprising:
at least one vibration source configured to generate a steady-state vibration in the tissue;
a three dimensional (3D) ultrasound probe configured to acquire a set of image data over a time period, the image data representing a thin volume of a tissue including a desired cross-sectional plane and at least two adjacent planes adjacent to said desired plane;
circuitry communicative with the ultrasound probe to receive the image data therefrom and comprising a processor with a memory having programmed thereon steps and instructions for execution by the processor to:
computationally estimate a time varying estimated displacement of tissue for each of a plurality of spatial points in said thin volume wherein at least one of the spatial points is located on each of the cross-sectional plane and the adjacent planes; and
adjust the time varying estimated displacements to compensate for phase differences among the estimated displacements for different ones of the spatial points, the phase differences resulting from differences in times at which the image data corresponding to the different ones of the spatial points were acquired, the adjusting causing phases of the plurality of time varying estimated displacements to be synchronized relative to a common reference time; and
computationally determine said at least one mechanical property of the tissue on the desired cross-sectional plane by using said plurality of phase-synchronized estimated displacements, wherein the number of adjacent planes is selected such that said at least one mechanical property of the tissue can be computationally determined within a real time refresh rate; and
a display device communicative with the circuitry to receive and display one or more images of the desired cross-sectional plane and said determined at least one mechanical property of the tissue within the real-time refresh rate.

16. An elastography system according to claim 15, wherein said image data comprises a plurality of RF-lines, and the circuitry is configured to record the time of acquisition for each of the plurality of RF-lines.

17. An elastography system according to claim 15, wherein said image data comprises a plurality of RF-lines, and said ultrasound probe is configured to acquire the RF-lines one-by-one with equal time intervals.

18. An elastography system according to claim 15, wherein said image data comprises a plurality of RF-lines and said at least one vibration source and said ultrasound probe are configured in a manner that the steady-state vibration is synchronized with the acquisition of the RF-lines, so that each RF-line is acquired at a constant delay with respect to the period of vibration.

19. An elastography system according to claim 15, wherein said at least one vibration source is configured to generate a harmonic sinusoidal excitation.

20. An elastography system according to claim 15, wherein said at least one vibration source is configured to generate a steady-state vibration that is a sum of multiple sinusoidal excitations with different frequencies, and different amplitudes and phases.

21. An elastography system according to claim 20, wherein said image data comprises a plurality of RF: lines, said at least one vibration source is configured to generate the steady-state vibration such that the frequencies of the excitations share a common period; and
said ultrasound probe is configured to acquire the RF-lines in synchronization with the common period, a rational fraction or an integer multiple of the common period.

22. An elastography system according to claim 15, wherein the ultrasound probe comprises a transducer array and a motor configured to drive said transducer array.

23. An elastography system according to claim 15, wherein the ultrasound probe comprises a 2D matrix of transducers.

24. An elastography system according to claim 15, wherein the vibration source is an electromagnetic voice coil.

25. An elastography system according to claim 15, wherein the vibration source is hand-held.

26. An elastography system according to claim 15, wherein the vibration source is mounted on an adjustable arm.

27. An elastography system according to claim 26, wherein the arm is mounted on an ultrasound machine, a patient bed, or a portable pole.

28. An elastography system according to claim 15, wherein the vibration source and the ultrasound probe are integrated together.

29. An elastography system according to claim 15, wherein said at least one vibration source comprises plural vibration sources configured in a manner that the location, direction and number of the vibration sources in contact with the tissue can be changed, keeping at least one vibration source in contact with tissue.

30. An elastography system according to claim 15, wherein the processor comprises at least one graphics processing unit and memory.

31. An elastography system according to claim 15, wherein the processor comprises at least one digital signal processor and memory.

32. An elastography system according to claim 15, wherein said at least one mechanical property includes any one or more properties selected from absolute elasticity, absolute shear modulus, absolute shear wave speed, and absolute viscosity.

33. An elastography system according to claim 15, wherein said at least one mechanical property is calculated from said estimated displacements by using any one or a combination of finite element method, local frequency estimators, travelling wave expansion and direct inversion.

34. An elastography system according to claim 15, wherein said ultrasound probe is configured to acquire said thin volume in a manner that the thin volume has extents of the volume in the desired plane larger than an extent of the volume in a third dimension perpendicular to the desired plane by a factor of at least 3.

* * * * *